United States Patent
Giontella

(10) Patent No.: US 9,993,361 B2
(45) Date of Patent: Jun. 12, 2018

(54) DYNAMIC ORTHOSIS FOR FOOT DROP

(71) Applicant: MP SRL, San Casciano Val di Pesa (IT)

(72) Inventor: Massimo Giontella, Florence (IT)

(73) Assignee: MP S.R.L. IN CONCORDATO PREVENTIVO, San Casciano Val di Pesa (IT)

( * ) Notice: Subject to any disclaimer, the term of this patent is extended or adjusted under 35 U.S.C. 154(b) by 245 days.

(21) Appl. No.: 14/652,360

(22) PCT Filed: Dec. 16, 2013

(86) PCT No.: PCT/IB2013/060973
§ 371 (c)(1),
(2) Date: Jun. 15, 2015

(87) PCT Pub. No.: WO2014/097107
PCT Pub. Date: Jun. 26, 2014

(65) Prior Publication Data
US 2015/0335459 A1 Nov. 26, 2015

(30) Foreign Application Priority Data
Dec. 17, 2012 (IT) ................ FI2012A0285

(51) Int. Cl.
*A61F 5/01* (2006.01)
*A61F 2/68* (2006.01)

(52) U.S. Cl.
CPC .......... *A61F 5/0113* (2013.01); *A61F 5/0127* (2013.01); *A61F 2002/6863* (2013.01);
(Continued)

(58) Field of Classification Search
CPC .... A61F 5/0113; A61F 5/0127; A61F 5/0102; A61F 5/0111; A61F 5/0118;
(Continued)

(56) References Cited

U.S. PATENT DOCUMENTS 6,171,272 B1 * 1/2001 Akita .................... A61F 5/0127
602/27
8,939,924 B1 * 1/2015 Paulos .................. A61F 5/0102
602/16
(Continued)

FOREIGN PATENT DOCUMENTS

| DE | 102010019355 | 11/2011 |
|---|---|---|
| GB | 720512 | 12/1954 |
| WO | 94200049 | 9/1994 |

OTHER PUBLICATIONS

English Abstract of DE102010019355.

*Primary Examiner* — Alireza Nia
*Assistant Examiner* — Rachel Berezik
(74) *Attorney, Agent, or Firm* — Preston Smirman; Smirman IP Law, PLLC

(57) ABSTRACT

Dynamic orthosis for drop foot, with a vertical flat, rigid bar connected to a collar of a patient's leg, and whose lower free end is connected to a bearing which is positioned in front of the internal malleoulus of the user and to constitute the joint of a cantilevered arm whose free end is connected to a bracket for the foot, and whose motion required for lifting the foot during deambulation is obtained by the force generated by a magnetic spring with the interposition of a rod, wherein the required lifting force are produced by a plurality of magnets, vertically aligned in a cylindrical sheath, and with the same polarity being juxtaposed to allow using their mutual repulsive forces.

9 Claims, 4 Drawing Sheets

(52) U.S. Cl.
CPC .......... *A61F 2005/0169* (2013.01); *A61F 2005/0179* (2013.01)

(58) Field of Classification Search
CPC ...... A61F 5/0123; A61F 5/0125; A61F 5/013; A61F 2005/0139; A61F 2005/0146; A61F 2005/0155; A61F 2005/0167; A61F 2005/0169; A61F 2005/0179; A61F 2002/5004; A61F 2210/009; A61F 2002/6863; A61F 2002/745; A61H 1/0266; A61H 1/0277; A61H 1/0218; A61H 1/0237; A61H 1/0262; A61H 1/02; A61H 3/00; A61H 3/008; A61H 2201/12; A61H 2201/1207; A61H 2201/1246; A61H 2201/164; A61H 2201/1642; A61H 2205/12; A63B 21/00192; A63B 21/005; A63B 21/0051
See application file for complete search history.

(56) References Cited

U.S. PATENT DOCUMENTS

| | | | | |
|---|---|---|---|---|
| 2004/0030275 A1* | 2/2004 | Morinaka | ............. | A61F 5/0125 602/27 |
| 2005/0054959 A1* | 3/2005 | Ingimundarson | .... | A43B 13/026 602/5 |
| 2007/0010772 A1* | 1/2007 | Ryan | ............. | A61F 5/0123 602/26 |
| 2012/0143112 A1* | 6/2012 | Tomiyama | ........... | A61F 5/0125 602/27 |

* cited by examiner

DYNAMIC ORTHOSIS FOR FOOT DROP

TECHNICAL FIELD

The invention refers to those orthosis intended to make up for the loss of functionality of the paralyzed muscles in drop foot and to allow a correct walking thereof.

STATE OF THE ART

It is known that the paralysis is the loss of the capacity of movement of a body segment. The paralyses can be divided into central and peripheral according to whether the first or second neuron of motion is affected.

Central paralyses caused by ictus, tumors, infectious neurologic, systemic diseases and others, after a first stage of muscle hypotonia, evolve in the majority of the cases to an increase of the muscle tone (hypertonia), so that they are called spastic paralyses. One characteristic thereof is the presence of clones, that is, global involuntary and non-oriented movements of a limb as a consequence of an alteration of the motion schemes.

Peripheral paralyses caused by herniated vertebral discs, tumors, degenerative disease of the second neuron and others, are always accompanied by muscle hypotonia and hypotrophy, so that they are called flabby paralyses, and the total loss of motor schemes causes problems for their functional recovery.

In almost the whole of foot paralyses a double deficit is caused: 1) loss of function of foot's dorsal flexor muscles, so that, in the step phase corresponding to the detachment of the limb from the ground, there occurs the drop of the foot that rubs onto the ground thereby preventing the walking, and 2) the partial or total loss of functionality of foot's pronator muscles (eversion muscles) with a predominance of the supinator muscles (invertors). All this, from a biomechanical point of view, is cause for a frontal offset of the ankle upon the lifting of the limb from the ground, thereby altering seriously the successive rest phase of the foot.

An automatic response to the deficit of the foot's dorsal flexion is an increment of the hip's flexion upon the lifting phase of the limb, but the vicarious effect is not sufficient, is quite demanding for the patient and, besides, it does not change the pathologic inter-rotation of the ankle.

In order to obviate to the serious functional deficits of the ambulation, many types of orthosis have been designed which, with different mechanisms, lift up the drop foot during walking.

In particular, the orthosis of AFO (Ankle Foot Orthosis) type are characterized by the use of an elastic system for moving the drop foot, so that they are commonly called "springs".

The drawback of all the elastic systems presently known, lies in the sudden and anti-physiological thrust exerted for lifting the foot upon detachment thereof from the ground, a thrust which, if it is ill supported in case of flabby paralysis, becomes counterproductive in case of spastic paralysis inasmuch as it induces an increase of the muscle hypertonia and the onset of pathologic clones. Moreover, all these elastic systems are disposed in the posterior side of leg and foot and are unable to control the inversion of the ankle.

Object of the Invention

The object of the invention is to propose a dynamic orthosis of AFO-type for the drop foot, which orthosis is able to provide functional and temporal characteristics as close as possible to those of a normal foot upon walking and, moreover, to avoid, in the central paralyses, not only the hypertonia and pathologic clones but also to oppose the onset thereof. The dynamic orthosis for the drop foot includes a vertical flat, rigid bar connected to a collar of a patient's leg, and whose lower free end is connected to a bearing which is positioned in front of the internal malleolus of the user and to constitute the joint of a cantilevered arm whose free end is connected to a bracket for the foot, and whose motion required for lifting the foot during deambulation is obtained by the force generated by a magnetic spring with the interposition of a rod, wherein the required lifting force are produced by a plurality of magnets, vertically aligned in a cylindrical sheath, and with the same polarity being juxtaposed to allow using their mutual repulsive forces. The loading phase of the spring corresponds to the pressure of the foot onto the ground and, therefore, to the maximum moment onto the malleoulus exerted by the compression of the magnets upon the movement thereof close to each other. The next release phase of the spring, that is, the spontaneous movement of the magnets away from each other, which takes place upon the detachment of the foot from the ground, i.e., when the moment onto the malleoulus is minimum, causes a clockwise rotation of the arm and, consequently, the lifting of the bracket along with the foot.

Possible Advantages

The advantages of the invention lie essentially in that it allows: lifting the foot from below during the launching of the leg; allowing the adjustment of the acting force, and adaptability to various sizes of the leg, all this with a high level of wellbeing due to a modest weight, optimal sanitary properties and suitability of use even for long periods of time, simple applicability inside the shoe, accurate permanent positioning of the foot and relevant support, protection of the toes and, after the step, with the foot brought again backward by moving the heel close to the static position.

DETAILED DESCRIPTION OF ONE EMBODIMENT OF THE INVENTION

The orthosis of the present invention is shown for reference in the accompanying drawings, wherein.

Figure 1:
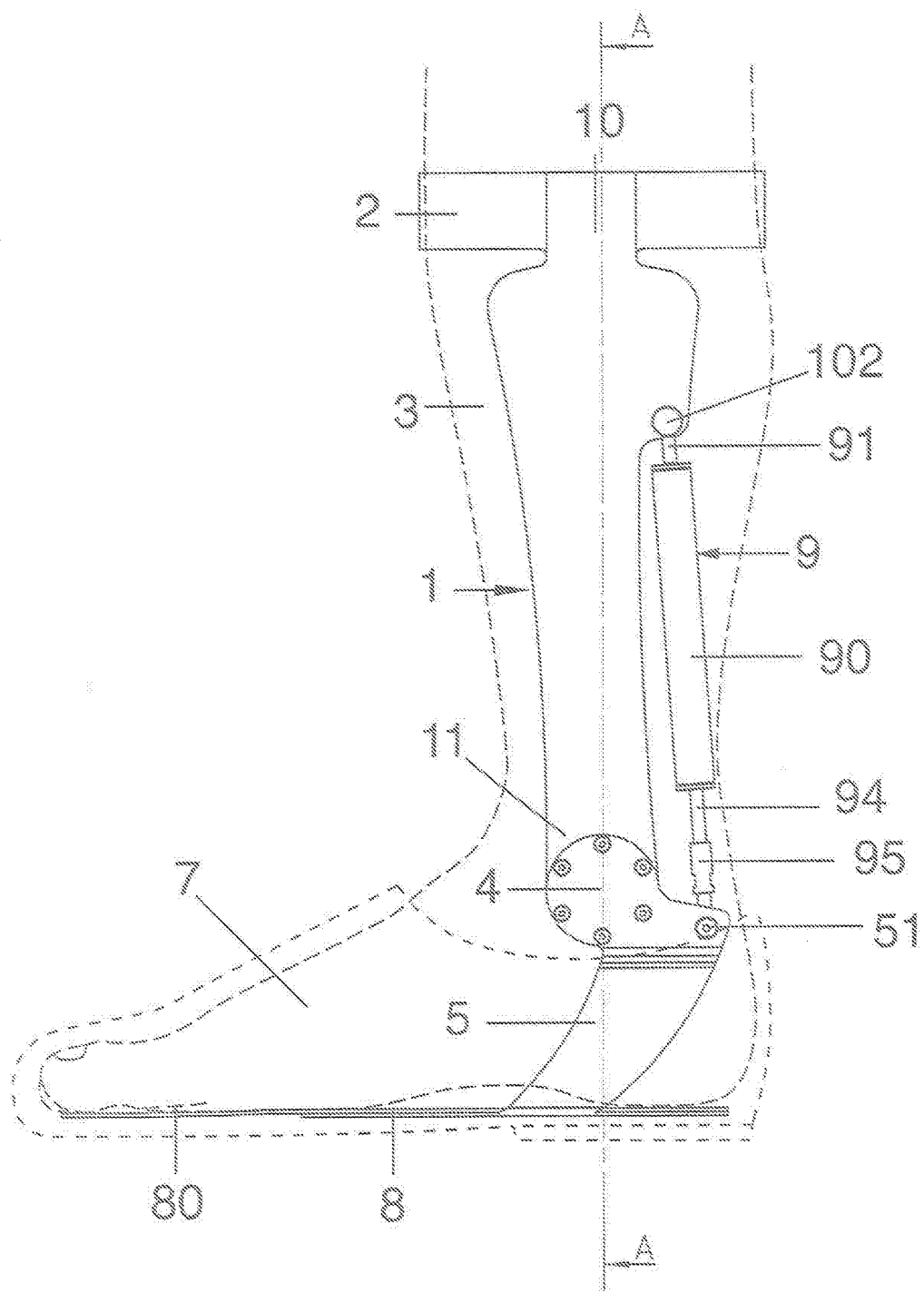
FIG. 1 is an ensemble front view of the orthosis in the state of use.
Figures 2, 3:
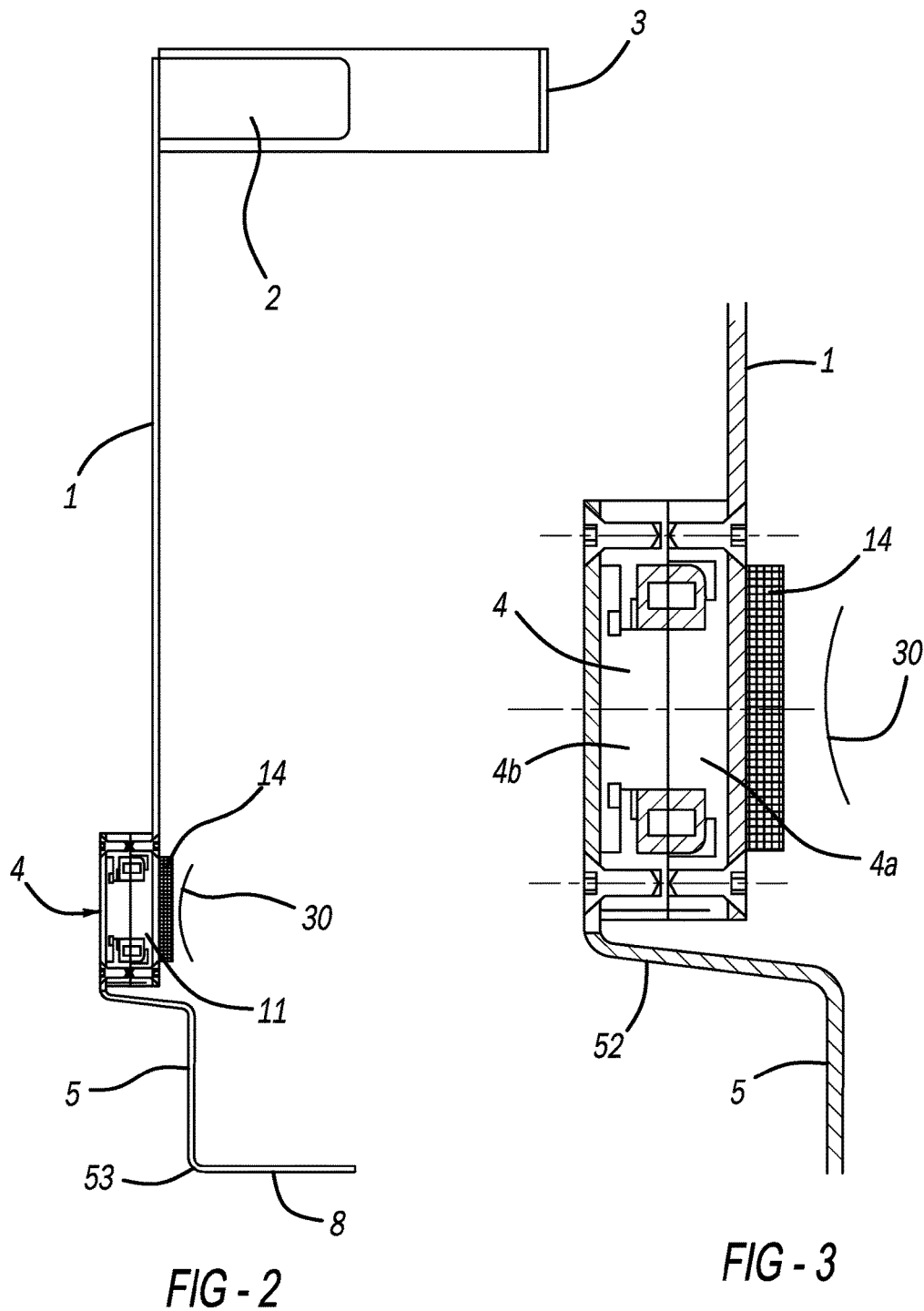
FIG. 2 is a vertical section taken on line A-A of FIG. 1.
FIG. 3 shows the primary joint for moving the foot.

Reduced to its essential construction, the orthosis comprises: a vertical, substantially flat bar (1), whose upper end (10) is anchored to a collar (2) to be fastened by common automatic means to the leg (3) above the user's calf, and fixed to the lower end of said bar is a rolling bearing (4) to which a flat cantilevered arm with curvilinear profiled arm (5) is hinged to be oscillated perpendicular to the leg at the level of the internal malleolus, that is, the protuberance belonging to the tibiotalar of the foot and projecting from the leg up to a higher and forward position with respect to the external malleolus.

More particularly, said bar (1) exhibits its lower part (11) integral to the fixed part (4a) of the bearing (4), has a decreasing width as it gets closer to the bearing (4), and is provided with a disc of soft-elastic material (14) for the protection of the malleolus (30). Moreover, said arm (5) has its upper end (52) shaped as a zee projecting transversally from the arm (5) and intended for connection with the rotating part (4b) of the bearing (4), while its lower end (53) is integral to the bracket (8) for a user's foot and forming a right angle therewith.

In particular, said bracket (8) extends lengthwise only for the region of the hind-foot and mid-foot, thus leaving the toes free, the elastic lifting of the latter being adequately provided by a polyethylene lamina (80) extended throughout the sole of the foot and fixed to the bracket (8).

Alternatively, said bracket (8) is possibly made of nylon by molding, for example, along the whole length of the foot, with sections of different thickness or made by different operating modes so as to result rigid in the region of hind-foot and mid-foot but elastic in the region of the toes.

In addition, the bracket (8) can be extended up to partially wrap the heel and the outer side of the foot. In this way the bracket houses the foot and is better bound to it with advantages for the comfort of the orthosis.

Moreover, in addition to the collar (2), further fastening means for fastening the orthosis to the leg could be provided. For instance, for some spastic paralysis a VELCRO™ fastening member can be arranged at the level of the ankle.

Obviously, this kind of devices have to be light-weighted and comfortable to wear, so in preferred embodiments of the invention the various members, such as the flat bar (1), the rolling bearing (4), the profiled arm (5) and the bracket (8) are shaped and sized so as to be as far as possible not bulky and weighty. In this view also the material of the above members becomes important and it is preferably chosen among composite materials such as materials of carbon fiber.

The elastic device (9) used for the present orthosis is a magnetic spring which utilizes the repulsion force of a plurality of magnets whose total magnetic field is equal, according to the principle of superimposition of effects, to the sum of the individual magnetic fields.

More in particular, and reference being made to the accompanying drawings, said magnetic spring comprises:—a cylindrical sheath (90) articulated on top by means of an extension (91) and a bush (102) of bar (1), made of any non-ferromagnetic material, and intended to hold a plurality of magnets (92) equal to each other, piled up with the same juxtaposed polarity and suitably spaced apart, which magnets have the function of generating the force Fs necessary to lift the drop foot during the ambulation: their subsequent loading being achieved by a forced mutual approach, during the same ambulation, through a piston (93) axially movable within said sheath and disposed on top of a rod (94) coming out of the bottom of the sheath and being in turn articulated to the bush (51) of said arm (5) with the interposition of an adjustment element (95) having the length of the rod (94).

The Operation is as Follows

The approach phase of magnets (92) takes place when, during walking, at the end of each step, the patient's foot is in the compression phase onto the ground, which corresponds to the maximum moment onto the malleolus (30).

In this state, the rod (94) and the piston (93) therewith will cause a compression for the mutual approach of magnets (92) (FIG. 1).

Figures 4, 5:
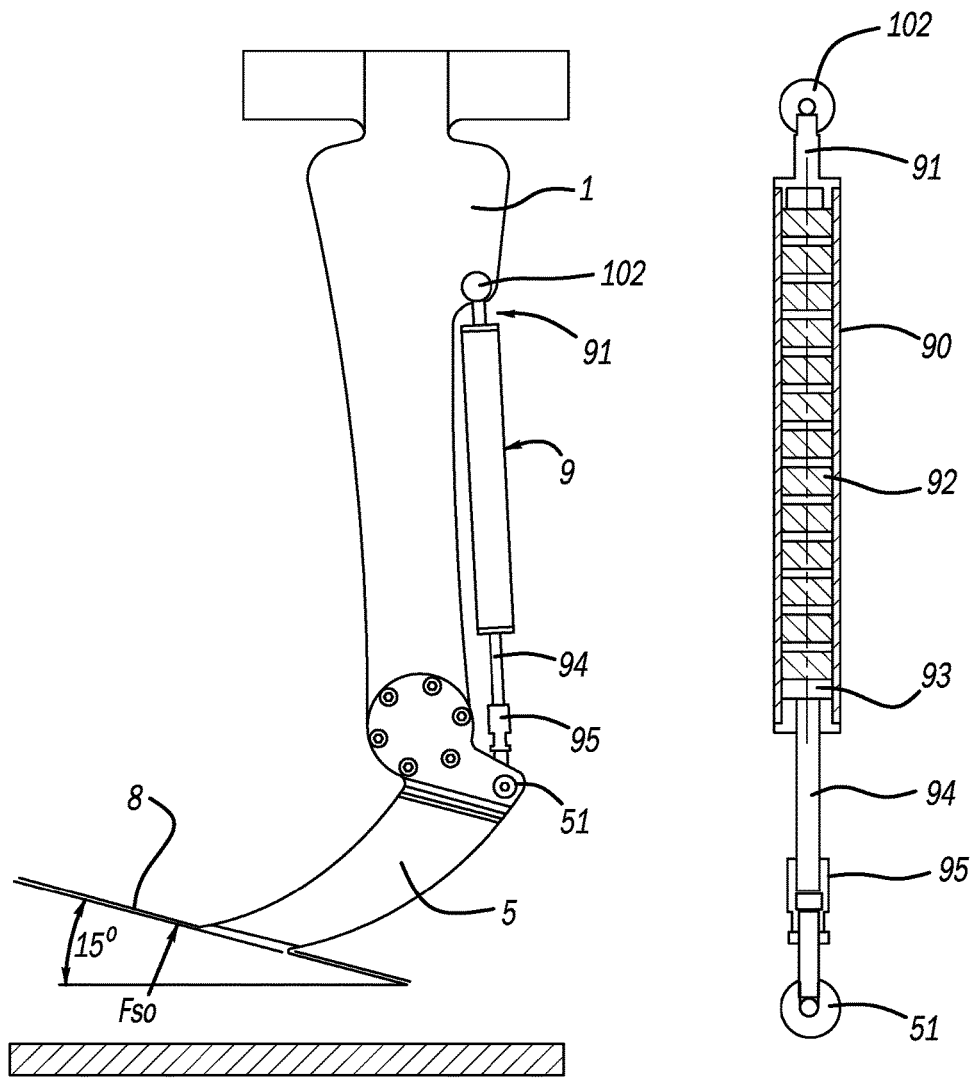
FIG. 4 shows the orthosis with the bracket in a state of maximum lifting.
FIG. 5 shows the elastic device.

The subsequent elongation phase, that is, the mutual and spontaneous moving of the magnets away from each other, takes place as soon as the patient's foot is detached from the ground, that is, when the moment on the malleolus is minimum. In this state, the arm (5) forced by the rod (94) to rotate clockwise, lifts up the bracket (8) along with the foot (FIG. 4).

Technical Characteristics of the Magnetic Spring

The magnetic spring of the elastic device (9) is made up of 13 disc-shaped magnets (92) having a diameter d=12 mm and thickness s=6 mm, and intended to exert a magnetic force Fm=3900 g in order to provide a lifting force $F_{SO}$=2600 g for the drop foot corresponding to the sum of Fp (weight of the foot)+Fs (weight of the shoe)+Fm (weight of the muscle component)+Fo (weight of the orthosis).

Said magnets are obtained in the axial magnetization direction from a material of neodymium-iron-boron by sinterization of N 48 quality. For a fine adjustment of the lifting force, Fso, the element (95) allows varying the useful length of the rod (94), thereby varying the distance of the magnets from each other.

Figure 6:
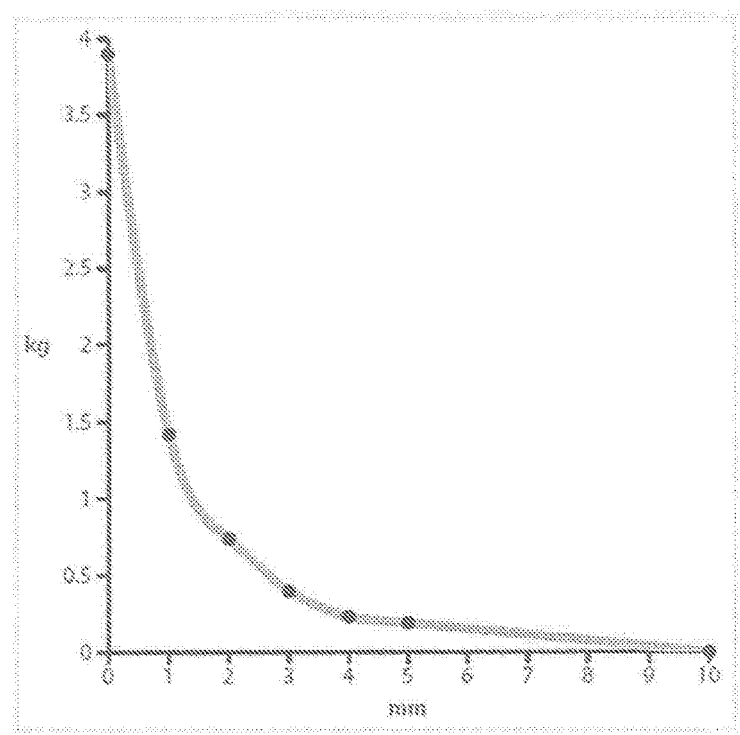
FIG. 6 shows a diagram of the elongation curve of a magnetic spring comprised in the device of the invention.

The elongation curve of said magnetic spring is shown in FIG. 6.

Figure 7:
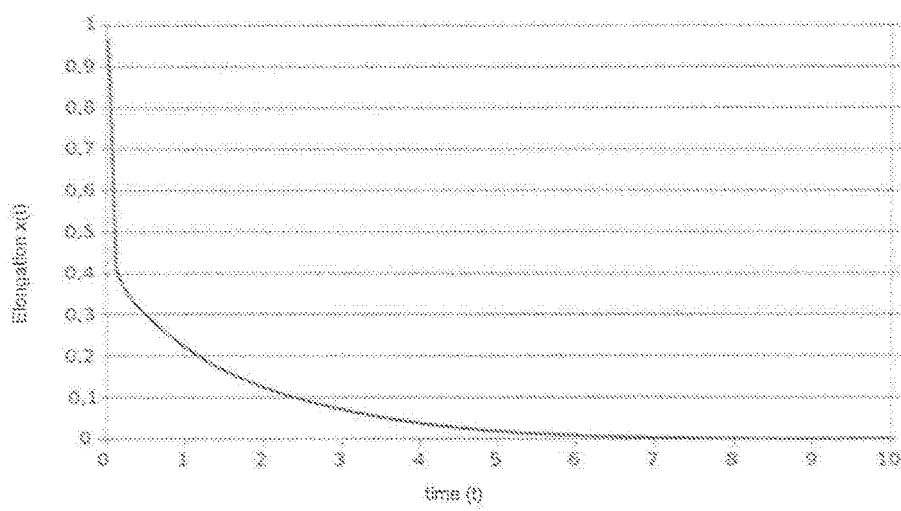
FIG. 7 shows a diagram of a elongation curve of a standard steel spring.

By comparing it with the curve relevant to the elongation of a steel spring, shown in FIG. 7, and comparing the 10 units of time of this figure with the travel in mm of FIG. 6, it can be observed that, while in the steel spring, 60% of the release force takes place in 1/100 of unit of time, in the present magnetic spring the same 60% of Fs which lifts the drop foot takes place in half the unit of time and, therefore, with an acceleration which is 50 times lower.

This is the reason why the lifting movement of the drop foot obtained by the present orthosis results truly physiological.

The invention claimed is:

1. A dynamic orthosis for treatment of a drop foot of a wearer, comprising:
   a flat, vertically oriented bar;
   a collar adapted to extend about a wearer's leg, wherein an upper end of the bar is connected to the collar;
   a rolling bearing, wherein a lower end of the bar is connected to the rolling bearing;
   an arm;
   wherein the rolling bearing is adapted to extend in a vertical plane proximate to a surface of a malleolus of the wearer's leg, and forming an articulation with the arm extending in a plane parallel to that of the bar and oscillating in both directions;
   a flat, horizontally oriented bracket;
   wherein the arm is connected to the bracket and is operable to lift the drop foot from below by a clockwise rotation of the arm thus lifting up the bracket;
   a magnetically moveable spring whose lifting force Fs is obtained by a plurality of magnets, each of the magnets being equal to each other and having a same juxtaposed polarity; and
   wherein the magnetically moveable spring comprises:
      a cylindrical sheath articulating with an upper portion of the bar by means of a first bush, wherein the plurality of magnets are contained completely within the cylindrical sheath; and
      a piston vertically movable on top of a rod articulating with the rolling bearing by means of a second bush.

2. The orthosis according to claim 1, wherein forced movement of each of the magnets close to each other for obtaining loading of the magnetically moveable spring is operated by the wearer through his or her leg with drop foot and body weight upon a final stage of a step, that is, with a foot under compression onto the ground.

3. The orthosis according to claim 1, wherein the lifting force Fs is in its release stage upon a foot detachment from the ground, increases with an acceleration 50 times less than that of a steel spring and allows the foot to be lifted in a physiologic manner.

4. The orthosis according to claim 1, wherein the rod of the magnetically moveable spring is provided with an adjustment element.

5. The orthosis according to claim 1, wherein the bracket is adapted to extend over a length not including toes of a foot, a lifting of the toes during walking being provided by an insole superimposed to the bracket and made up of a polyethylene lamina extending throughout a sole of the foot.

6. The orthosis according to claim 1, wherein the bracket is adapted to extend over a foot's whole length and is molded in nylon, with sections of various thickness or formed with different operating modalities so as to result in being rigid on a back foot and midfoot portion of the foot, but elastic on a forefoot portion of the foot.

7. The orthosis according to claim 1, wherein the lower end of the bar is provided with a disc of soft-elastic material that is adapted for protection of the malleolus.

8. The orthosis according to claim 1, wherein the collar is adapted to be fixed to the wearer's leg, above a calf portion of the leg, by automatic means.

9. The orthosis according to claim 1, wherein the arm and bracket for the drop foot are of such dimensions as to allow introduction thereof into a shoe.

\* \* \* \* \*